United States Patent [19]

Strauss

[11] Patent Number: 4,664,654
[45] Date of Patent: May 12, 1987

[54] AUTOMATIC PROTRACTING AND LOCKING HYPODERMIC NEEDLE GUARD

[76] Inventor: Eric C. Strauss, 2505 Killarney Way, Modesto, Calif. 95355

[21] Appl. No.: 837,146

[22] Filed: Mar. 7, 1986

[51] Int. Cl.[4] .............................................. A61M 5/32
[52] U.S. Cl. .................................................. 604/198
[58] Field of Search ........................ 604/192, 197, 198

[56] References Cited

U.S. PATENT DOCUMENTS

| | | |
|---|---|---|
| 2,876,770 | 10/1955 | White . |
| 2,925,083 | 2/1960 | Craig ................................... 604/198 |
| 3,884,230 | 5/1975 | Wulff ................................... 604/198 |
| 4,356,822 | 10/1980 | Winstead-Hall . |
| 4,425,120 | 1/1984 | Sampson . |
| 4,573,976 | 3/1986 | Sampson ............................. 604/263 |

*Primary Examiner*—John D. Yasko

[57] ABSTRACT

A tool to protect professionals who use hypodermic needles in their work from inadvertent punctures to themselves by contaminated needles comprising a sliding member (16) and a stationary member (28). The first step in using this tool is to retract sliding member (16) by compressing protruding member (24 left and 24 right) together thereby reducing the overall width of (24). (24) is then manipulated into channel (26) and retracted to the point to where leaf (18) can be depressed. The user then allows spring (30) to protract sliding member (16), beveled edge (17) of leaf (18) will then catch in groove (19), the purpose being to expose the tip (41) of tube (42) while maintaining sliding member (16) in an unlocked position. The user can then puncture the outer dermis or layer of the subject without meeting obstruction from sliding member (16). Once the surface of the subject has been punctured, the user advances the needle whereby sliding member (16) is then compressed into stationary member (18), as the needle is advanced and sliding member (16) is compressed, leaf (18) is dislodged from groove (19) and springs back to its original position thus assuring no obstruction to the protraction of sliding member (16) as the needle is withdrawn. When the needle is withdrawn, sliding member (16) protracts back to its original pre-retracted position. As protrusion (24) reaches notch (36), protrusion (24 right) will re-expand to its pre-compressed width and lock into notch (36). As an added safety feature, protrusion (24 right) has a bevel shaped corner (38) that engages with an indentation (37) that is shaped to receive corner (38), thus further assuring that sliding member (16) can not accidently be disengaged from its locked position. Following use, the entire device with the needle safely enclosed, is disposed of in the proper receptacle.

1 Claim, 6 Drawing Figures

U.S. Patent  May 12, 1987  4,664,654
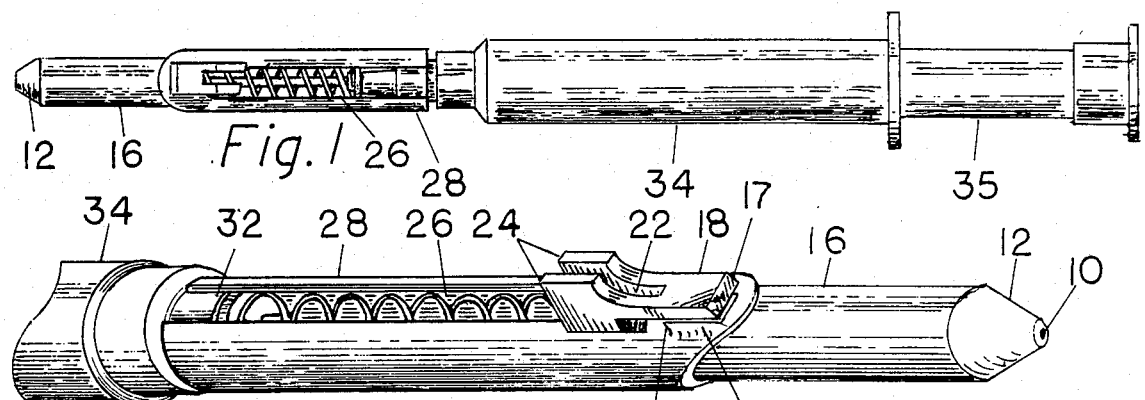
Fig. 1
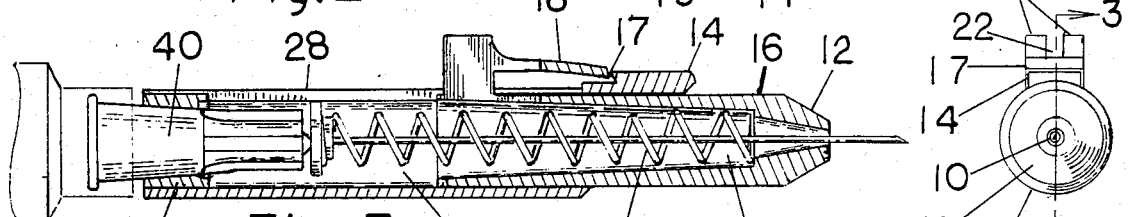
Fig. 2
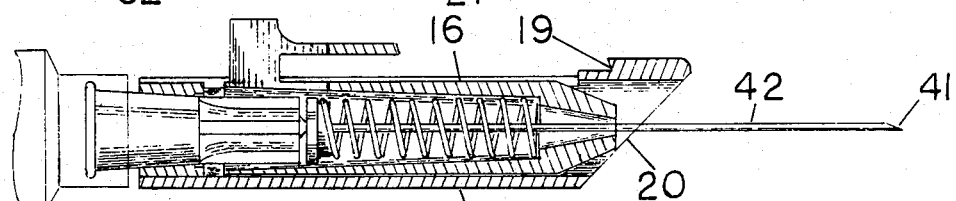
Fig. 3a
Fig. 4
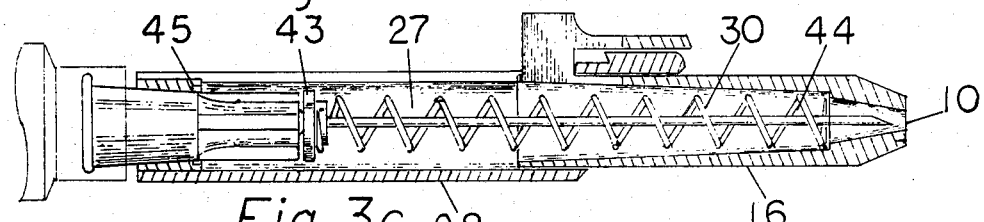
Fig. 3b
Fig. 3c
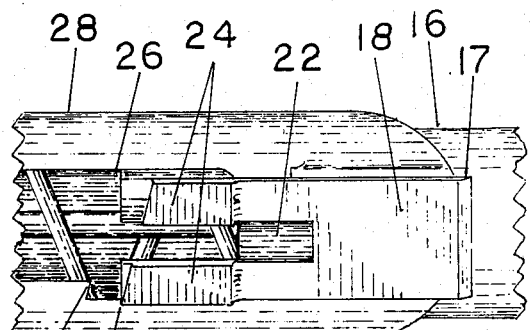
Fig. 5
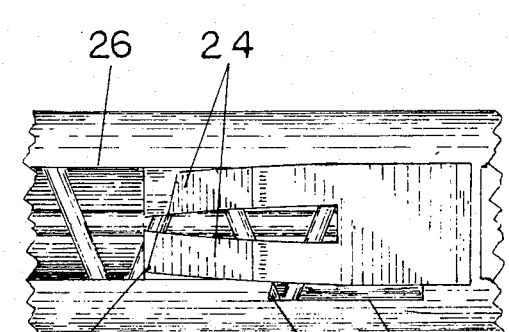
Fig. 6

AUTOMATIC PROTRACTING AND LOCKING HYPODERMIC NEEDLE GUARD

BACKGROUND—FIELD OF INVENTION

This invention pertains to the medical and science fields. Specifically, it is a safety device to protect users of hypodermic needles from inadvertent punctures from contaminated needles.

BACKGROUND—DESCRIPTION OF PRIOR ART

Present practice among professional people when disposing of hypodermic needles consists of the following:
1. Recapping the needle in the plastic cap provided and then disposing of it, or
2. Breaking off the sharp end of the needle in a cutting device, or
3. Disposal of the contamined needle and syringe into a special receptacle provided for this purpose Such techniques are unsatisfactory in that the contaminated needle is left exposed between the time it is removed from the subject or contaminate source and the point at which the aforementioned methods of disposal are performed. During this period of time in which the contaminated needle is exposed, the user is susceptible to injury and possible infection by said needle. Therefore, each time an injection is given or blood is drawn, the user is exposed to the possibility of a localized introduction of pathogens via an accidental puncture from a contaminated hypodermic needle. This invention was designed with the purpose of preventing such inadvertent accidents from occurring.

This invention is designed to be safely used in regards to subject safety. This invention is designed to be easily understood and used by health care workers and other professional users of hypodermic needles. This invention has been designed in such a manner as to make its safety providing mechanism work automatically; thereby, excluding the human element common to most accidents.

OBJECTS AND ADVANTAGES

Accordingly I claim the following objects and advantages of this invention: to provide professional persons a means of safely using hypodermic needles within their work place, to provide these means without significantly changing current practices and to provide for these safety means to function automatically on the withdrawing of the hypodermic needle from the surface layer of the punctured subject.

Furthermore, I claim the design of this invention incorporates a locking mechanism that will automatically lock the safety sheath in a position that completely encloses the needle after it is withdrawn from the subject. I claim that as the hypodermic needle is being withdrawn, that the safety sheath is protracting synchronously, thus ensuring the tip of the contaminated needle will be enclosed in the confinements of the safety sheath at approximately the same instance the needle loses contact with the subject's surface and that the safety sheath will lock automatically within that same instance, thus providing safe handling during disposal of the needle. This advantage greatly removes any chance of an accident occurring from a subject who may move or jerk during the time of the puncture.

Furthermore, as an added safety factor, I claim the locking mechanism of the invention must be manually manipulated to unlock, thereby decreasing the possibility of an accidental disengagement of the safety sheath during the time of disposal. Also, I claim that for the safety and comfort of the subject of the puncture, that the tip of the hypodermic needle (approximately three sixteenths inch) can be exposed from the needle tip end of the safety sheath prior to puncture to allow the user of the needle to puncture through the layer of skin of the subject before any resistance (approximately one pound per inch) from the spring of the safety device is met, thus providing for safe introduction of the needle into the subcutaneously layer of the skin.

Interested parties who study this invention will find the aforementioned objects and advantages further outlined in the following descriptions and drawings.

DRAWING FIGURES

FIG. 1 shows a top view of the invention attached to a syringe.

FIG. 2 shows a perspective, elevational view of a two sectional piece tool according to the invention with said tool being shown as it would be attached to a syringe.

FIG. 3a shows a sectional view of FIG. 2 from the side with the invention in its set position exposing the tip of the needle as the invention would appear prior to puncturing the subject.

FIG. 3b shows a sectional view of FIG. 2 with one section fully retracted into the other as it would appear when the needle is advanced as far as it could be, according to this invention, into the subject.

FIG. 4 shows a straight forward frontal view of the tool of FIG. 3c.

FIG. 3c shows a sectional view of FIG. 2 with the needle entirely enclosed, as the tool of this invention would appear in its locked position.

DRAWING REFERENCE NUMERALS 10 hole in tip of 12
12 truncated cone
14 prominence of 28
16 body of sliding member
17 beveled tip of 18
18 flexible leaf extension of 24
19 groove of engagement of 17
20 angular end of 28
22 slot of 24
24 left and right protruding members of 16
26 channel in 28
27 cavity of 28
28 body of stationary member
30 spring
32 sleeve to receive 40
34 syringe body
35 syringe plunger
36 notch of 26
37 bevel shaped indention to receive 38
38 beveled edge of 24 right
40 hub of 42
beveled tip of 42
42 tube extending from 40 to 41
43 securing means of washer for one end of 30
44 tapered cavity for securing one end of 30
45 recess for numeral 43

TWO SECTIONAL PIECED TOOL—DESCRIPTION

FIG. 1 shows a two sectional pieced tool according to the preferred embodiment of the invention with such tool connected to a syringe 34 and 35 to illustrate how the invention would appear when ready for use.

The tool of FIG. 1 comprises two sections shown as 28 and 16. Preferably, these sections are made of plastic. 28 is the larger of the two sections (approximately one and three fourths inch) and is the stationary member. 16 is the smaller member (approximatey one and one fourth inch) and is the sliding member.

FIG. 2 shows a perspective observational view of the tool of this invention with the sliding member 16 fully protracted to the point in which the tip of the needle is covered.

FIG. 3a shows a sectional view from the side of the invention of FIG. 2 with the body of the sliding member (16) set in a slightly retracted position to expose the end of the needle. FIG. 3b shows a sectional view from the side of the invention of FIG. 2 with the body of the sliding member (16) fully retracted into the body of the stationary member (28).

FIG. 3c shows a sectional view from the side of the invention of FIG. 2 with the body of the sliding member (16) fully protracted beyond the tip of the needle.

FIG. 4 shows a straight forward frontal view of FIG. 3c.

FIG. 5 shows a close up fragmented view from the top looking down at the locking mechanism of the invention of FIG. 2 in its locked position.

FIG. 6 shows a close up fragmented view from the top looking down at the locking mechanism retracted into the channel.

The two sectional pieced tool of FIG. 2 is a safety device used with hypodermic needles when drawing venous or arterial blood and when giving intravenous, intramuscular, and subcutaneous injections. According to the embodiment of the invention, the safety device and needle could by obtained as a unit.

The tool of FIG. 2 provides safe means of handling hypodermic needles following removal of 41 from the surface layer of the subject of the puncture. These safety means are designed to work automatically so as to reduce the risk of injury to the user.

The tool of FIG. 2 comprises two generally cylindrical shaped members, a stationary member (28) and a sliding member (16). To use the tool of FIG. 2, the user first unlocks 16 from 36 by compressing 24 left and 24 right together thereby reducing the width of 24. The user can then retract 24 into channel 26 against spring 30, as illustrated in FIG. 6. This action serves the purpose of exposing tip 41 of tube 42 about three sixteenths inch, as illustrated in FIG. 3a. To hold 16 in channel 26 the user depresses leaf 18 and allows spring 30 to protract leaf 18 thereby enaging beveled end 17 of leaf 18 into groove 19 thus holding 24 in 26 to expose 41, as illustrated in FIG. 3a. With tip 41 exposed the user can proceed to puncture 41 through the surface layer of the subject. The user will discover on advancing the needle further that 16 will be compressed into 28 against tension provided by spring 30 and the user will note flexible leaf 18 will spring back to its resting position, as illustrated in FIG. 3b. When removing the needle the user will note that as he or she withdraws the needle 16 is protracted forward by spring 30. As 16 protracts, protrusion 24 is guided along channel 26. Once protrusion 24 is juxtaposed to notch 36 protrusion 24 expands back to its pre-retracted width and 24 right locks into notch 36 with beveled edge 24 right engaging with 37 providing added assurance that 16 will remain locked. After using this device once, the user would then dispose of the entire device into the appropriate receptacle.

The scope of this tool has been presented here to illustrate how such a device is used in the drawing of blood and the giving of injections. To summarize, this invention is intended to protect the user against contamination from any fluid that the needle comes into contact with and therefore, its use could be beneficial to fields other than medicine.

I claim:

1. A device, comprising a sectional shield that encloses a hypodermic needle and includes an outer member that receives an inner, sliding member with means for said sliding member to be shiftably set in a retracted position against a forward biasing pressure means and a channel on said outer member as means to engage with a rearward mounted vertical projection on said sliding member and a vertical slot in said projection to provide a width reducing means to engage said projection into said channel and a width, re-expansion providing means on said channel for same said projection to provide securing means from said inner sliding member in a forward position that extends beyond the tip of said needle and means to hold said projection of said sliding member in said re-expansion means against any inadvertent rearward biasing force applied to said sliding member.

* * * * *